United States Patent
Ohishi et al.

(10) Patent No.: US 6,920,195 B2
(45) Date of Patent: Jul. 19, 2005

(54) RADIOGRAPHIC IMAGE FORMING APPARATUS AND RADIOGRAPHIC IMAGE FORMING METHOD

(75) Inventors: Atsushi Ohishi, Musashino (JP); Kazuyoshi Ottomo, Hino (JP); Yasushi Nakano, Hino (JP)

(73) Assignee: Konica Corporation, Tokyo (JP)

( * ) Notice: Subject to any disclaimer, the term of this patent is extended or adjusted under 35 U.S.C. 154(b) by 132 days.

(21) Appl. No.: 10/422,819

(22) Filed: Apr. 25, 2003

(65) Prior Publication Data

US 2003/0202631 A1 Oct. 30, 2003

(30) Foreign Application Priority Data

Apr. 30, 2002 (JP) .................................... 2002-128239

(51) Int. Cl.[7] ................................................ H05G 1/60
(52) U.S. Cl. ............................ 378/10; 378/19; 378/20
(58) Field of Search ........................... 378/4, 9, 10, 16, 378/19, 20, 95, 196, 197; 250/581–586

(56) References Cited

U.S. PATENT DOCUMENTS

| | | | | |
|---|---|---|---|---|
| 4,439,866 A | * | 3/1984 | Kato et al. | 378/19 |
| 4,472,822 A | * | 9/1984 | Swift | 378/10 |
| 4,485,481 A | * | 11/1984 | Takano | 378/19 |
| 5,233,193 A | * | 8/1993 | Arakawa | 250/580 |
| 5,590,167 A | * | 12/1996 | Arai | 378/38 |
| 5,654,555 A | * | 8/1997 | Buytaert et al. | 250/581 |
| 5,832,051 A | * | 11/1998 | Lutz | 378/8 |
| 6,072,855 A | * | 6/2000 | Arakawa | 378/98.11 |
| 6,148,058 A | * | 11/2000 | Dobbs | 378/19 |
| 6,470,068 B2 | * | 10/2002 | Cheng | 378/20 |
| 6,781,603 B2 | * | 8/2004 | Tanaka | 345/690 |

* cited by examiner

Primary Examiner—Allen C. Ho
(74) Attorney, Agent, or Firm—Finnegan, Henderson, Farabow, Garrett & Dunner, L.L.P.

(57) ABSTRACT

A radiographic image forming apparatus having a radiation source for irradiating conical radiation to a test body; a stimulable phosphor plate, arranged opposite to the radiation source with the test body sandwiched in-between for recording an intensity of radiation having passed through the test body; a rotation/displacement section for relatively rotating and displacing the radiation source with respect to the test body, by placing the test body at a rotation center; a radiation controller for controlling a radiation from the radiation source; a recording section for recording at least one sinogram into the stimulable phosphor plate by the radiation; a reading section for reading a sinogram recorded by the recording section; and an image processing section for forming a two-dimensional or three-dimensional tomographic image by reconstructing a sinogram read by the reading section.

16 Claims, 4 Drawing Sheets

ROTATION ANGLE 0 DEG.

FIG. 3(b)

SLIT TRAVEL DISTANCE 0 mm

FIG. 4(a)

ROTATION ANGLE 10 DEG.

FIG. 4(b)

SLIT TRAVEL DISTANCE 0.2 mm

FIG. 5(a)

ROTATION ANGLE 200 DEG.

RADIOGRAPHIC IMAGE FORMING APPARATUS AND RADIOGRAPHIC IMAGE FORMING METHOD

BACKGROUND OF THE INVENTION

The present invention relates to a radiographic image forming apparatus and radiographic image forming method, and particularly to the formation of a two-dimensional or three-dimensional tomographic image of a test body.

PRIOR ART

In a medical field, a radiation CT (Computed Tomography) scanner is used. In this scanner, radiation is applied through the periphery of the body of a patient as a test body, and the radiation having passed through the test body is detected and is converted into an image signal. The image signal is subjected to reconfiguration processing, whereby a three-dimensional tomographic image of a biological substance is formed.

The CT scanner is commonly based on a helical scanning method where a radiation source and radiation detector are arranged as a pair with a test body sandwiched in-between, and are moved and rotated helically about the body axis of the test body around the test body to detect the intensity of radiation at many rotary positions. Another method of getting a tomographic image by rotating the test body is also proposed.

In the aforementioned computed tomography method, a technique is also developed where a conical radiation called cone beam is generated from the radiation source and is applied to the test body in a two-dimensional form; then the FPD (Flat Panel Detector)—a multi-channel detector—or an X-ray camera is used as a radiation detector to provide two-dimensional detection of radiation, thereby reconstructing a three-dimensional tomographic images. Further, an X-ray television technique is also developed, where high speed detection of radiation is provided by the aforementioned multi-channel detector and a three-dimensional image is reconstructed; then reconstructed three-dimensional tomographic image is displayed as a moving image on the screen, thereby finding out the site to be radiographed, while checking the image.

In the meantime, there is a widespread use of the CR (Computed Radiography) where radiation is applied to the test body in a two-dimensional form, and radiation energy in response to radiation transmittance of each portion of the test body is subjected to two-dimensional accumulation into the stimulable phosphor plate. This stimulable phosphor plate is scanned by excitation beam so that the accumulated radiation energy is emitted as fluorescent light, which undergoes photoelectric conversion to get image signals.

PROBLEMS TO BE SOLVED BY THE INVENTION

In the aforementioned computed tomography where the CT scanner rotates, high speed rotation is essential and a lager-scale scanner must be built. This requires high costs and a substantial installations space. So this method has not been often used in a smaller hospital or clinic. According to this method, furthermore, radiographs of a test body are taken helically while the scanner is moving along the body axis, and resolution in the axial direction and isotropy are reduced. Thus, a three-dimensional image may not be reconstructed from a two-dimensional tomographic image, with the result that the diagnostic capacity may be reduced, according to this prior art method.

Further, when radiation as a cone beam is applied, much light scattering occurs, depending on the type of a test body since the cone beam irradiates a wide range at one time. This has been one of the causes for image noise. What is more, it is less economical to use the FPD or X-ray camera as a radiation detector for two-dimensional detection of radiation. When the X-ray camera is used, the gray scale that can be represented is limited. This has been the cause for a reduced diagnostic capacity.

This object of the present invention is to provide a low-cost and space-saving radiation image forming apparatus that produces a two-dimensional or three-dimensional tomographic image of high picture quality based on CR technologies.

SUMMARY OF THE INVENTION

The aforementioned problem can be solved by the following arrangements:

(1) A radiographic image forming apparatus comprising:

a radiation source for applying conical radiation to a test body;

a stimulable phosphor plate arranged opposite to this radiation source with the test piece sandwiched in-between, and designed for recording the intensity of radiation passing through this test body; and rotation/displacement means for relative rotation and displacement of the radiation source and test body about the test body.

This radiographic image forming apparatus is characterized by further comprising:

radiation control means for controlling the application of radiation from the radiation source;

recording means for recording one or more sinograms on the stimulable phosphor plate by application of the radiation;

reading means for reading this recorded sinogram, and image processing means for forming a two-dimensional and three-dimensional tomographic image by reconstructing the read sinogram.

(2) A radiographic image forming apparatus according to the aforementioned item (1) further characterized in that:

a radiation shield plate equipped with a multiple slits orthogonal to the body axis of the test body is arranged between the test body and the stimulable phosphor plate;

the radiographic image forming apparatus is further equipped with traveling means for moving the radiation shield plate along the body axis of the test body for each rotation and displacement by the rotation/displacement means, and this recording means records the radiation as a transmitted image into the stimulable phosphor plate for every rotation and displacement, this radiation being the one having passed through the slits of the radiation shield plate having been moved.

(15) A radiographic image forming method in a radiographic image forming apparatus comprising:

a radiation source for applying conical radiation to a test body;

a stimulable phosphor plate arranged opposite to this radiation source with the test piece sandwiched in-between, and designed for recording the intensity of radiation passing through this test body; and rotation/displacement means for relative rotation and displacement of the radiation source and test body about the test body;

This radiographic image forming method is characterized by further comprising:

a step of controlling the application of radiation from the radiation source;

a step of recording one or more sinograms on the stimulable phosphor plate by application of the radiation;

a step of reading the recorded sinogram(s); and a step of forming a two-dimensional or three-dimensional tomographic image by reconstructing the read sinogram(s).

According to the inventions described in the aforementioned (1), (2) and (15), conical radiation is applied to the test body by relative rotation and displacement of the test body and radiation source, and the radiation shield plate is moved along the body axis of the test body for each rotation and displacement. Then the radiation for each rotation and displacement having passed through the test body and through the slits of the radiation shield plate is recorded on the stimulable phosphor plate as a sinogram along the body axis. The recorded sinogram is read and a two-dimensional or three-dimensional tomographic image is formed by its reconstruction. This arrangement provides a two-dimensional or three-dimensional tomographic image of high picture quality with reduced image noise resulting from scattered light, by using a CR apparatus in widespread use. It provides a low-cost and space-saving radiographic image forming apparatus characterized by improved diagnostic capacity.

(3) A radiographic image forming apparatus described in item (1) further comprising:

a pair of radiation shield plates provided with multiple slits orthogonal to the test body installed between the radiation source and test body, and between the test body and stimulable phosphor plate to ensure that they will be matched to the positions of the slits of the pair of radiation shield plates; and traveling means for synchronizing the pair of radiation shield plates for each rotation and displacement by the rotation/displacement means, and moving these plates along the body axis of the test body;

wherein the radiation having passed through the slits of the moved pair of radiation shield plates is recorded on the stimulable phosphor plate as transmitted image for each rotation and displacement by this recording means.

According to the description in item (3), a pair of radiation shield plates is installed between the radiation source and test body, and between the test body and the stimulable phosphor plate so that the slit positions are matched. The pair of radiation shield plates is synchronized for each rotation and displacement and is moved along the body axis of the test body. The radiation having passed through the test body and the slits of the pair of radiation shield plates is recorded on the stimulable phosphor plate as a transmission image for each rotation and displacement. This arrangement reduces the image noise caused by scattered light, and minimizes the exposure dose of the test body, thereby allow a high-quality two-dimensional and three-dimensional tomographic image to be produced.

(4) A radiographic image forming apparatus described in items (2) and (3) characterized in that the traveling means moves the radiation shield plates along the body axis of the test body 0.2 mm or more for each rotation and displacement (5) A radiographic image forming apparatus described in items (2) and (3) characterized in that spacing between slits of the radiation shield plate is 5 mm or more.

According to the arrangement shown in items (4) and (5), the traveling distance of the radiation shield plate along the body axis for each rotation and displacement is 0.2 m or more, and spacing between slits of the radiation shield plate is 5 mm or more. This arrangement ensures that each of multiple transmission images constituting the sinogram stored on the stimulable phosphor plate does not practically overlap the other. Hence it provides an adequate margin to the space for recording a transmission image for each rotation and displacement, thereby providing a two-dimensional and three-dimensional tomographic image of high picture quality.

(6) A radiographic image forming apparatus described in item (1) further comprising transfer means for transferring to external equipment on the network the sinogram read by the reading means; wherein the image processing means is an image forming apparatus connected via the network and a two-dimensional or three-dimensional tomographic image is formed by reconstructing the sinogram transmitted through the transfer means.

(7) A radiographic image forming apparatus described in item (6) further characterized in that the image forming apparatus is connected to a plurality of transfer means via the network and a two-dimensional or three-dimensional tomographic image is formed by reconstructing each of the sinograms transmitted through multiple transfer means.

(8) A radiographic image forming apparatus described in item (6) or (7) comprising:

input means for inputting the result of diagnosis of the two-dimensional or three-dimensional tomographic image formed in the above step; and transfer means for transferring the result of diagnosis input in the above step together with the two-dimensional or three-dimensional tomographic image via the network to the source from which the sinogram has been sent.

According to the invention shown in items (6), (7) and (8), the image forming means is an image forming apparatus connected to a plurality of transfer means. It reconstructs each of the sinograms transferred via the network and forms each two-dimensional or three-dimensional tomographic image. It sends the image together with the input result of diagnosis via the network to the source from which the sinogram has been sent. This arrangement permits a shared use of the image forming apparatus for forming a two-dimensional or three-dimensional tomographic image, thereby ensuring a lower cost. This arrangement also provides the result of diagnosis together with the image, with the result that the diagnostic capacity is improved.

(9) A radiographic image forming apparatus described in item 1 further characterized in that the rotation/displacement means ensures that the overall amount of rotation and displacement does not exceed 360 degrees when the radiation source and test body are relatively rotated and displaced about the test body.

(10) A radiographic image forming apparatus described in item (1) further characterized in that the rotation/displacement means rotates the test body, thereby causing relative rotation and displacement of the radiation source and test body about the test body.

According to the arrangements given in items (9) and (10), the test body is rotated without exceeding 360 degrees, and this action reduces the load of the test body and the installation space for the radiographic image forming apparatus.

(11) A radiographic image forming apparatus described in item (1) further characterized in that, when the radiation source and test body has been turned a predetermined amount of rotation and displacement by the rotation/displacement means, the radiation control means controls the radiation source for each rotation and displacement to apply radiation.

(12) A radiographic image forming apparatus described in item (11) further characterized in that the radiation control means to ensure that the predetermined amount of rotation and displacement does not exceed 10 degrees when it controls the radiation source to apply radiation.

According to the arrangement shown in items (11) and (12), radiation is applied intermittently every time the radiation source and test body are rotated and displaced by a predetermined amount. This arrangement minimizes the exposure dose of the test body. What is more, the predetermined amount of rotation and displacement does not exceed 10 degrees. This improves the resolution and provides a two-dimensional or three-dimensional image of high picture quality.

(13) A radiographic image forming apparatus described in item (1) further characterized in that the radiation control means controls the radiation source to apply radiation synchronously with the heartbeat of the test body.

According to the arrangement given in item (13), the radiation source is controlled to apply radiation synchronously with the heartbeat of a test body. This minimizes the variation within the body of the test body and provides recording of a sinogram consisting of transmission images under uniform conditions, thereby offering a two-dimensional or three-dimensional tomographic image of high picture quality.

(14) A radiographic image forming apparatus described in item (1) further characterized in that the radiation control means controls the amount of radiation applied by the radiation source in response to the rotation and displacement provided by the rotation/displacement means.

According to the arrangement described in item (14), the amount of radiation is controlled in response to the rotation and displacement. This makes it possible to record a sinogram where the amount of radiation is adjusted in response to changes in the thickness of the body of the test body resulting from the position for each rotation and displacement, thereby providing a two-dimensional or three-dimensional tomographic image of high picture quality.

DETAILED DESCRIPTION OF THE PREFERRED EMBODIMENTS

Embodiments of the Present Invention

The following describes the details of the preferred embodiments of the present inventions with reference to drawings:

The following describes a radiographic image forming system 100 as an embodiment of radiographic image forming apparatus according to the present invention.

The configuration will be described first.

Figure 1:
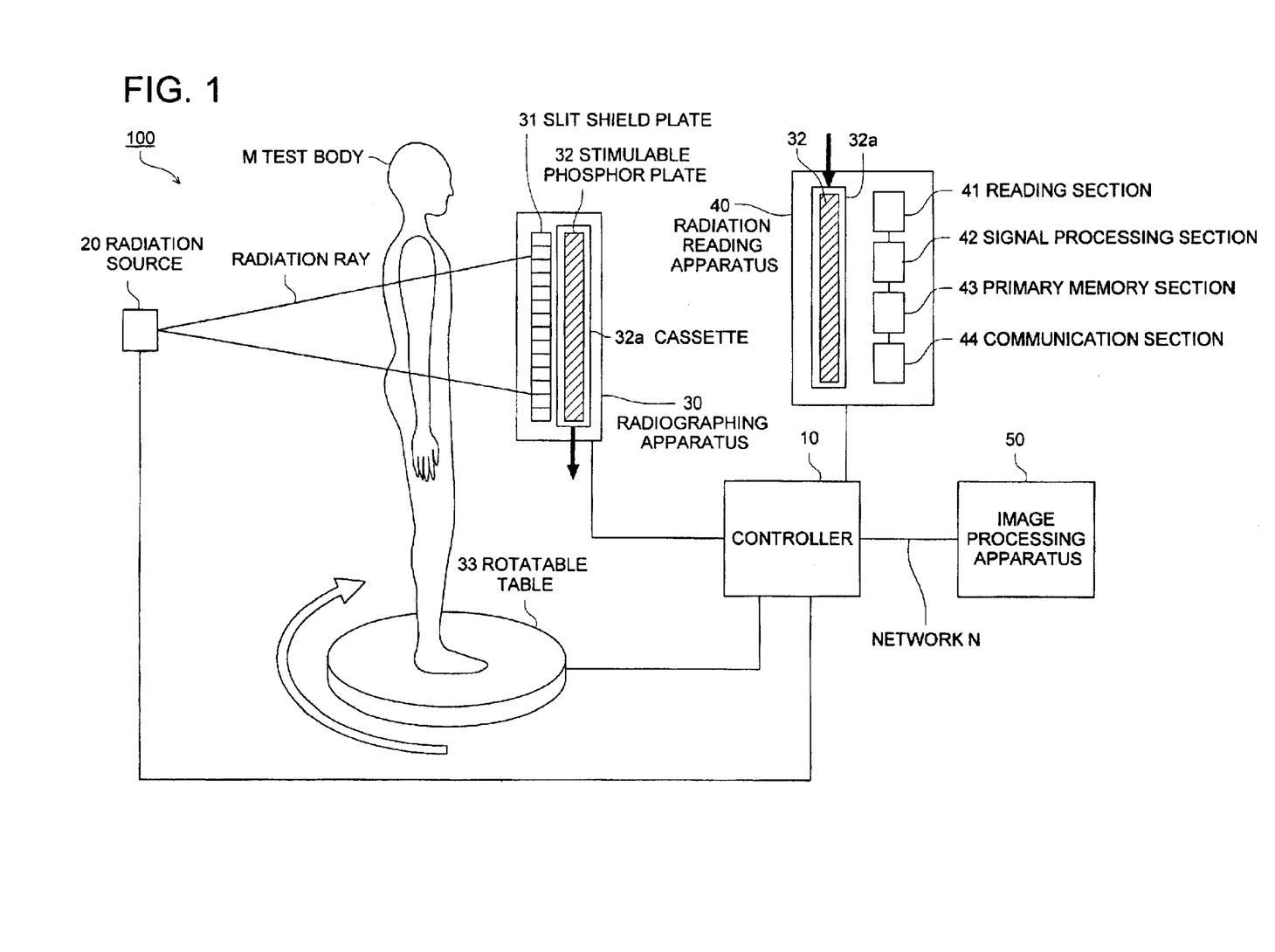
FIG. 1 is a conceptual diagram representing the entire configuration of s radiographic image forming system of the present invention.

FIG. 1 is a conceptual diagram representing the entire configuration of s radiographic image forming system 100.

In FIG. 1, the radiographic image forming system 100 comprises a controller 10, radiation source 20, rotatable table 33, radiographing apparatus 30, radiation reading apparatus 40 and image processing apparatus 50.

The controller and image processing apparatus 50 are connected with each other via the network N and can exchange data with each other. In the present embodiment, the following description, assumes that one controller 10 and one image processing apparatus 50 are connected via the network. The number of the controllers 10 connected to the image processing apparatus 50 via the network and the installation site thereof are not restricted.

The network N is a network to which various communications lines including the telephone line, leased line, mobile unit network, communications satellite network and CATV line can be applied. Various lines such as LAN (Local Area Network), WAN (Wide Area Network) and Internet can be applied to this network.

The radiation source 20, radiographing apparatus 30 and rotatable table 33 are connected to the controller 10 that controls the radiographic operation. The radiation reading apparatus 40 is connected to the controller 10, and is controlled by it.

The controller 10, radiation source 20, radiographing apparatus 30, rotatable table 33, radiation reading apparatus 40 are can be connected via the network. A leased line may be used for their connection based on the Interface standards including the SCSI.

The controller 10 comprises a CPU (Central Processing Unit) for controlling each section of the controlled items, a control panel for radiographing and a screen for displaying the result of radiographing (not illustrated). The radiation dose and irradiation timing at the radiation source 20, rotation of the rotatable table 33 and movement of the slit shield plate 31 in the radiographing apparatus 30 are controlled at the time of radiographing to provide synchronization of radiographing operation. In other words, the controller 10 performs the functions of the radiation control means for controlling the radiation source and the traveling means for traveling the radiation shield plate.

The controller 10 is provided with such a transmission means as a modem and router, and the sinogram image data entered from the communications section 44 of the radiation reading apparatus 40 is sent to the image processing apparatus 50 connected via the network. A two-dimensional or three-dimensional tomographic image of the radiographed sinogram image data is reconstructed, and the reconstructed tomographic image is received from the image processing apparatus 50.

The radiation source 20 applies radiation to the test body M in a conical form (as a cone beam) at the radiation dose and irradiation timing designated by the controller 10.

The image processing apparatus 50 comprises such a transmission line as a modem and router and reconstructs the sinogram image data sent from the controller 10 via the network N. It forms a two-dimensional tomographic image or a three-dimensional tomographic image by further reconstruction of the two-dimensional tomographic image, and sends it to the controller 10 from which the sinogram has been sent. In other words, the image processing apparatus 50 that serves as image processing means that reconstructs the sinogram at the radiographic image forming apparatus and form a three-dimensional tomographic image.

In this case, it is also possible that the formed two-dimensional or three-dimensional tomographic image is diagnosed by a doctor or a computerized diagnostic apparatus present on the side of the image processing apparatus 50, and the result of this diagnosis is input into the image processing apparatus 50 through such input means as an input key or communications interface. Then the result can be sent together with the aforementioned tomographic image.

The following describes the details of the individual units of the radiographing apparatus 30 and rotatable table 33 according to the present invention:

The radiographing apparatus 30 comprises a slit shield plate 31 and a stimulable phosphor plate 32 built in the cassette 32a.

Figure 2:
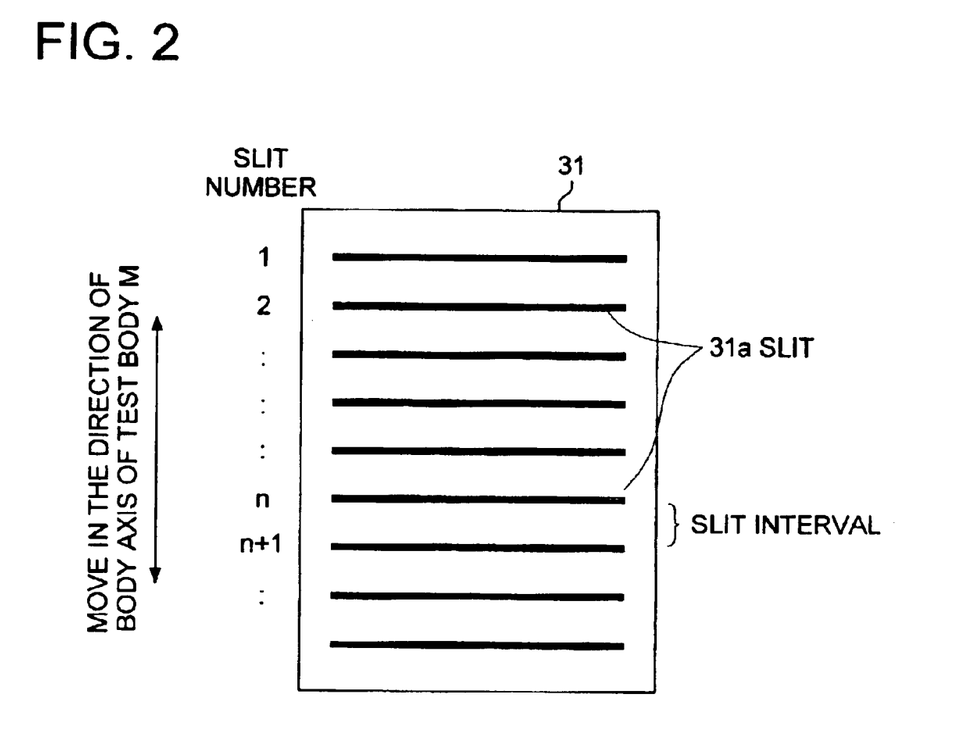
FIG. 2 is a front view of a slit shield plate 31 given in FIG. 1.

As the front view is shown in FIG. 2, the slit shield plate 31 is a radiation shield plate provided with multiple straight openings or slits 31a orthogonal to the body axis of the test body M. It is installed between the test body M and stimulable phosphor plate 32. The slit shield plate 31 is movable along the body axis of the test body M in the vertical direction, and is moved in the specified direction (either upward or downward) by the distance specified by the controller 10. Spacing between the slits 31a cannot be set as desired. For the sake of explanation in the present embodiment, it is assumed that the spacing between the slits 31a is set at 5 mm, and movement is allowed along the body axis in the downward direction.

The stimulable phosphor plate 32 is a plate with a photostimulated phosphor layer formed thereon. It absorbs and accumulates the radiation having passing through the test body M and slit shield plate 31, and records the sinogram of the test body M in response to the intensity of the radiation. The stimulable phosphor plate 32 is built in the cassette 32 as a casing, and the cassette 32a can be mounted or dismounted from the radiographing apparatus 30 and radiation reading apparatus 40. After the sinogram has been recorded on the stimulable phosphor plate 32, the cassette 32a is removed from the radiographing apparatus 30 and is put into the radiation reading apparatus 40. Then the recorded sinogram is read out as an image data.

In other words, the radiation source 20, slit shield plate 31 and stimulable phosphor plate 32 serves as a recording means for recording one or more sinograms of the test body.

The rotatable table 33 is formed in a rotatable disk carrying the test body M. It performs continuous rotation and displacement at the specified speed in response to the instruction for rotation given from the controller 10. In other words, the rotatable table 33 serves as a rotation/displacement means for rotating and displacing the test body and radiation source about the test body. In the present embodiment the amount of rotation and displacement will be given in angles.

The following describes the details of the radiation reading apparatus 40.

The radiation reading apparatus 40 comprises a reading section 41, signal processing section 42, primary memory section 43 and communications section 44.

The reading section 41 comprises an excitation light generator, photoelectric converter and others. The stimulable phosphor plate 32 built in the cassette is scanned by excitation light and the photostimulated light is subjected to photoelectric conversion to get the image signal in response to the intensity of the photostimulated light. This signal is sent to the signal processing section 42. In other words, the reading section 41 serves as reading means.

The signal processing section 42 comprises an analog-to-digital converter. It converts the input analog image signal into the digital image data and provides correction of shading and uneven sensitivity caused by the reading section 41. The result is stored in the primary memory section 43. The sinogram image data stored in the primary memory section 43 is output to the controller 10 through the communications section 44, and is sent to the image processing apparatus 50 by the controller 10.

Figures 3A, 3B:
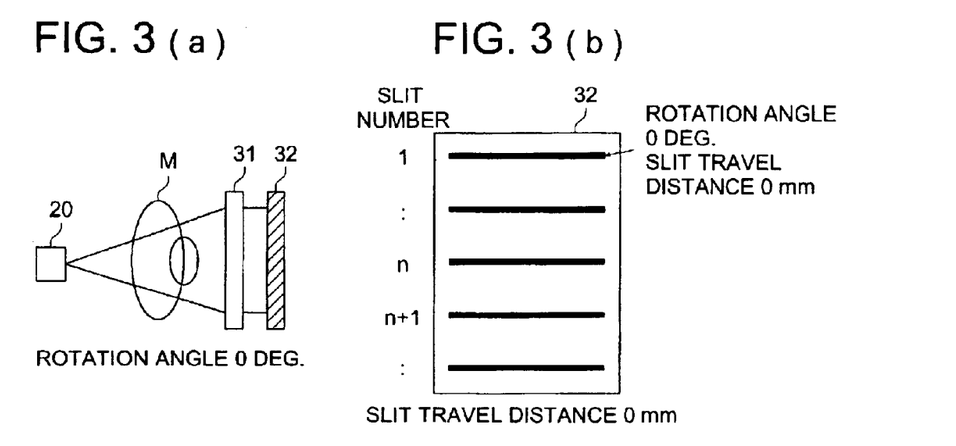
FIG. 3(a) is a drawing representing how a test body is radiographed at an rotary angle of 0 degree, as viewed from the head of a test body M.
FIG. 3(b) is a drawing showing a transmission image recorded on a stimulable phosphor plate 32 when radiographed under the same conditions as above.
Figures 4A, 4B:
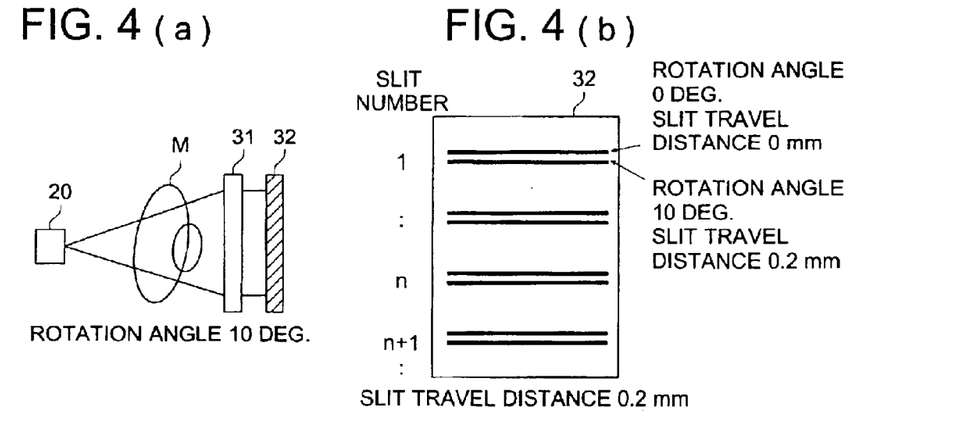
FIG. 4(a) is a drawing representing how a test body is radiographed at a rotary angle of 10 degrees, as viewed from the head of a test body M.
FIG. 4(b) is a drawing showing a sinogram consisting of a transmission image recorded on a stimulable phosphor plate 32 when radiographed under the same conditions as above.
Figures 5A, 5B:
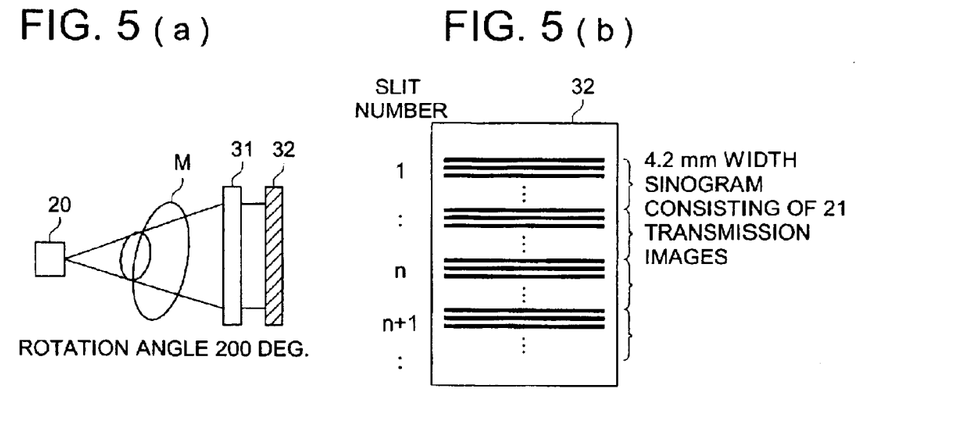
FIG. 5(a) is a drawing representing how a test body is radiographed at a rotary angle of 200 degrees, as viewed from the head of a test body M.
FIG. 5(b) is a drawing showing a sinogram consisting of a transmission image recorded on a stimulable phosphor plate 32 when radiographed under the same conditions as above.

The following describes the operation in the present embodiment:

FIGS. 3(a) through 5(b) shows the radiographing operation performed in the radiographic image forming system 100 according to the present invention. FIG. 3(a), FIG. 4(a) and FIG. 5(a) show how the test body M is radiographed at each rotary angle as viewed from the head of the test body M. FIG. 3(b) shows sinogram of the test body M radiographed in the state given in FIG. 3(a) and recorded on the stimulable phosphor plate 32, FIG. 4(b) shows the sinogram in the state given in FIG. 4(a), and FIG. 5(b) shows the sinogram in the state shown in FIG. (a).

To prepare for radiographing, the controller 10 sets the distance of slit movement on the slit shield plate 31 and the rotary angle of the rotatable table 33 to the default position, i.e. a slit movement of 0 mm and a rotary angle of 0 degree. Then upon receipt of an instruction from the operator when the test body M is positioned on the rotatable table 33, the rotatable table 33 starts rotation and displacement. At the same time, radiation is applied from the radiation source 20 in a cone beam at a slit movement of 0 mm and a rotary angle of 0 degree, and radiographs are taken, as shown in FIG. 3(a).

The radiation applied from the radiation source 20 and having passed through the test body M passes through the slit 31a provided on the slit shield plate 31. At this time, the scattered light caused by the test body M is removed by this slit shield plate 31. At the same time, the cone beam turns into a fan beam and is absorbed by the stimulable phosphor plate 32 and recorded as a transmission image.

In this case, the transmission image recorded on the stimulable phosphor plate 32 in the first radiographing operation is recorded at the position corresponding to the initial position of each slit of the slit shield plate 31, as shown in FIG. 3(b). It is preferred that radiographing should be performed while measuring the heartbeat of the test body M.

In order to minimize the fluctuation of the state in the body and to get uniform state, it is preferred that radiation application timing should be synchronized with the heartbeat of the test body M.

As shown in FIG. 4(a), the slit shield plate 31 is moved down 0.2 mm where the rotatable table 33 has rotated and displaced 10 degrees. Under this condition, radiation is applied from the radiation source 20, similarly to the above step. In this case, the transmission image having passing through the test body M and having been recorded on the stimulable phosphor plate 32 is recorded 0.2 mm downward for each slit number with respect to the default position where recording is made at a rotary angle of 0 and slip movement of 0 mm, as shown in FIG. 4(b).

As described above, where the rotatable table 33 is rotated and displaced at every rotary angle of 10 degrees, the slit shield plate 31 is fed 0.2 mm downward to take a radiograph. This arrangement ensures that the transmission image recorded for each slit number is recorded 0.2 mm downward on the stimulable phosphor plate 32. For example, when the rotatable table 33 is continuously rotated and displayed from 0 to 200 as shown in FIG. 5(a) and radiographs are taken a total of 21 times for each rotation/displacement at an rotary angle of 10 degrees during this time, a sinogram consisting of 21 transmission images for each slit number is recorded on the stimulable phosphor plate 32 as shown in FIG. 5(b). In this case, the slit movement is 0.2 mm for each rotation/displacement of 10 degrees, so the sinogram for each slit 31a is recorded in a width of about 4.2 mm.

The controller 10 controls the radiation source 20 in response to the rotary angle of the rotatable table 33, and adjusts the radiation dose to be generated. Adjustment is made in such a way that the strength of radiation of each transmission image constituting the sinogram will be uniform. For example, when the rotary angle is 0 degree and radiation is applied to the front (pectoral region) of the test body M from the back (back region), the thickness of the test body M is small, so adjustment is made to ensure that the radiation dose will be reduced. As the rotation/displacement is carried out gradually from the state shown in FIG. 3(a), the thickness of the test body M is increased to reach the maximum value when 90-degree rotation/displacement has been completed. In response to this, the radiation dose is gradually increased by adjustment. In other words, adjustment is made in such a way that radiation dose is increased gradually when the rotary angle is from 0 to 90 degrees and from 180 to 270 degrees. Adjustment is made so that radiation dose is reduced gradually when the rotary angle is from 90 to 180 degrees and from 270 to 360 degrees. The optimum radiation dose to be adjusted should be calculated in advance in response to rotation/displacement.

The above description is based on the assumption that the slit movement of the slit shield plate 31 is 0.2 mm at every rotation/displacement of the rotatable table 33 by 10 degrees. The rotary angle and slit movement for determining this radiographing position used in the above are each only one example. These values can be set at other appropriate values. However, if the slit movement is too much limited, the spacing of transmission image recorded on the stimulable phosphor plate 32 will be reduced, and adjacent transmission images will practically overlap each other. This may cause difficulties in reconstruction. To avoid this, it is preferred that spacing should be 0.2 mm or more. Similarly, if the spacing between each of slits 31a is too much limited, the spacing between each of transmission images recorded on the stimulable phosphor plate 32 will be reduced, and adjacent transmission images will practically overlap each other, and, at the same time, the number of the transmission images to be recorded will be limited. To avoid this problem, it is preferred that spacing should be 5 mm or more. Further, if the rotary angle for each radiographing is too big and resolution is deteriorated, then there will be only a limited amount of information for reconstructing the two-dimensional or three-dimensional tomographic image, with the result that resolution will be deteriorated. To prevent this, it is preferred that the rotary angle for recording a transmission image for each rotation/displacement by application of radiation should be 10 degrees or less.

Upon termination of the radiographing of the test body M as described above, the controller 10 causes the reading section 41 to read out multiple sinograms radiographed at each rotary angle and recorded on the stimulable phosphor plate 32. Then the image data of the read sinogram image is input from the communications section 44, and is sent to the image processing apparatus 50 via the network N.

The image processing apparatus 50 analyzes the received image data and identifies the image data of the sinogram for each slit 31a. To put it more specifically using the aforementioned example, the slit shield plate 31 is arranged so that the spacing between slits is 5 mm. Since the sinogram for each slit 31a is recorded at a width of 4.2 mm, an unoccupied area where the image data is not recorded is present for each slit 31a. Identifying this unoccupied area, the image processing apparatus 50 identifies the sinogram image data for each slit 31a.

Then the image processing apparatus 50 reconstructs the sinogram image data for each identified slit 31a, and forms a two-dimensional tomographic image for each spacing of the slit 31a. When a three-dimensional tomographic image is required, the image processing apparatus 50 further reconstructs the formed a two-dimensional tomographic image to form a three-dimensional tomographic image, and send it to the controller 10. For example, if the spacing of the slit 31a is 5 mm, a two-dimensional or three-dimensional tomographic image is formed for each 5 mm along the body axis. If a program is created in such a way that the formed three-dimensional tomographic image is diagnosed by a doctor or a computerized diagnostic apparatus present on the side of the image processing apparatus 50, and the result of this diagnosis is output to the controller 10 through input means, then the image processing apparatus 50 sends to the controller 10 the result of diagnosis together with the formed two-dimensional or three-dimensional tomographic image. The controller 10 receives the formed two-dimensional or three-dimensional tomographic image the result of diagnosis from the image processing apparatus 50 and completes tomographic image processing.

As described above, when the test body M is rotated and displaced by the rotatable table 33 and the rotatable table 33 has rotated and displaced by the specified amount, then the slit shield plate 31 equipped with multiple slits 31a orthogonal to the body axis of the test body M moves the specified distance along the body axis. At the same time, the radiation source 20 applies radiation in the conical form and the transmission image of the test body M for each specified rotation/displacement is recorded on the stimulable phosphor plate 32. When the radiation reading apparatus 40 has read the sinogram consisting of multiple transmission images, the read sinogram is sent to the image processing apparatus 50 by the controller 10. Then the image processing apparatus 50 reconstructs and forms the two-dimensional or three-dimensional tomographic image. This arrangement makes it possible to form a two-dimensional or three-dimensional tomographic image of high picture quality by making use of a CR scanner in widespread use, reader and radiation source. This makes a significant contribution to cost reduction and space saving.

Further, the slit shield plate 31 is a radiation shield plate capable of removing the scattered light and image noise even in the case of the cone beam characterized by a wide emission range. Further, a slit 31a is provided to move the slit shield plate 31 along the body axis for each rotation/displacement, whereby a sinogram consisting of multiple transmission images can be recorded on one stimulable phosphor plate 32.

Radiation is intermittently applied at every rotation/displacement of the test body M at each specified rotary angle at the time of radiographing, thereby allowing the exposure dose of the test body M to be minimized. Further, the heartbeat of the test body M is measured and the radiation application timing is synchronized with the measured heartbeat. This minimizes the deflection within the body of the test body M and provides recording of a sinogram consisting of transmission images under uniform conditions, thereby ensuring a two-dimensional or three-dimensional tomographic image of high picture quality. Further, the radiation dose is adjusted in response to the rotary angle, and this arrangement minimizes the variation in the radiation dose caused by the thickness of the test body M that varies according to the rotary angle, thereby providing a two-dimensional or three-dimensional tomographic image of high picture quality.

The rotatable table 33 is provided to allow rotation/displacement of the test body M at the time of radiographing. This arrangement permits use of the existing CR scanner and radiation source, and makes a significant contribution to cost reduction and space saving. The total amount of rotation/displacement required for formation of a two-dimensional or three-dimensional tomographic image does not exceed 360 degrees, namely, not exceed one rotation, thereby reducing the load of a patient as a test body M.

The sinogram read by the radiation reading apparatus 40 through the controller 10 is sent to the image processing apparatus 50 connected via the network, and it is possible to get a two-dimensional or three-dimensional tomographic image reconstructed by the image processing apparatus 50 and/or the result of diagnosis. Accordingly, a two-dimensional or three-dimensional tomographic image can be easily obtained even when the image processing apparatus 50 for reconstruction is not provided. At the same time, even if there is no doctor, the result of diagnosis is obtained easily. Further, the image processing apparatus 50 is capable of reconstructing the three-dimensional tomographic image sent from multiple controllers 10. This arrangement provides a less costly radiographic image forming system 100.

In a small-sized hospital or clinic without a doctor capable of reading the radiogram, it is possible to form a low-cost three-dimensional tomographic image high picture quality using the existing CR apparatus, while using no extra space. This improves the diagnostic capacity.

The description in the present embodiment based on an example of the radiographic image forming apparatus 100 according to the present invention, without being restricted thereto.

For example, in the above description, the slit shield plate 31 is moved in a predetermined direction with stimulable phosphor plate 32 locked at a specified position at the time of radiographing at each rotary angle, whereby the sinogram is recorded on the stimulable phosphor plate 32. Without being restricted thereto, it is also possible that the stimulable phosphor plate 32 is moved in a predetermined direction with the slit shield plate 31 locked at a specified position, thereby radiographing the test body at each rotary angle.

Figure 6:
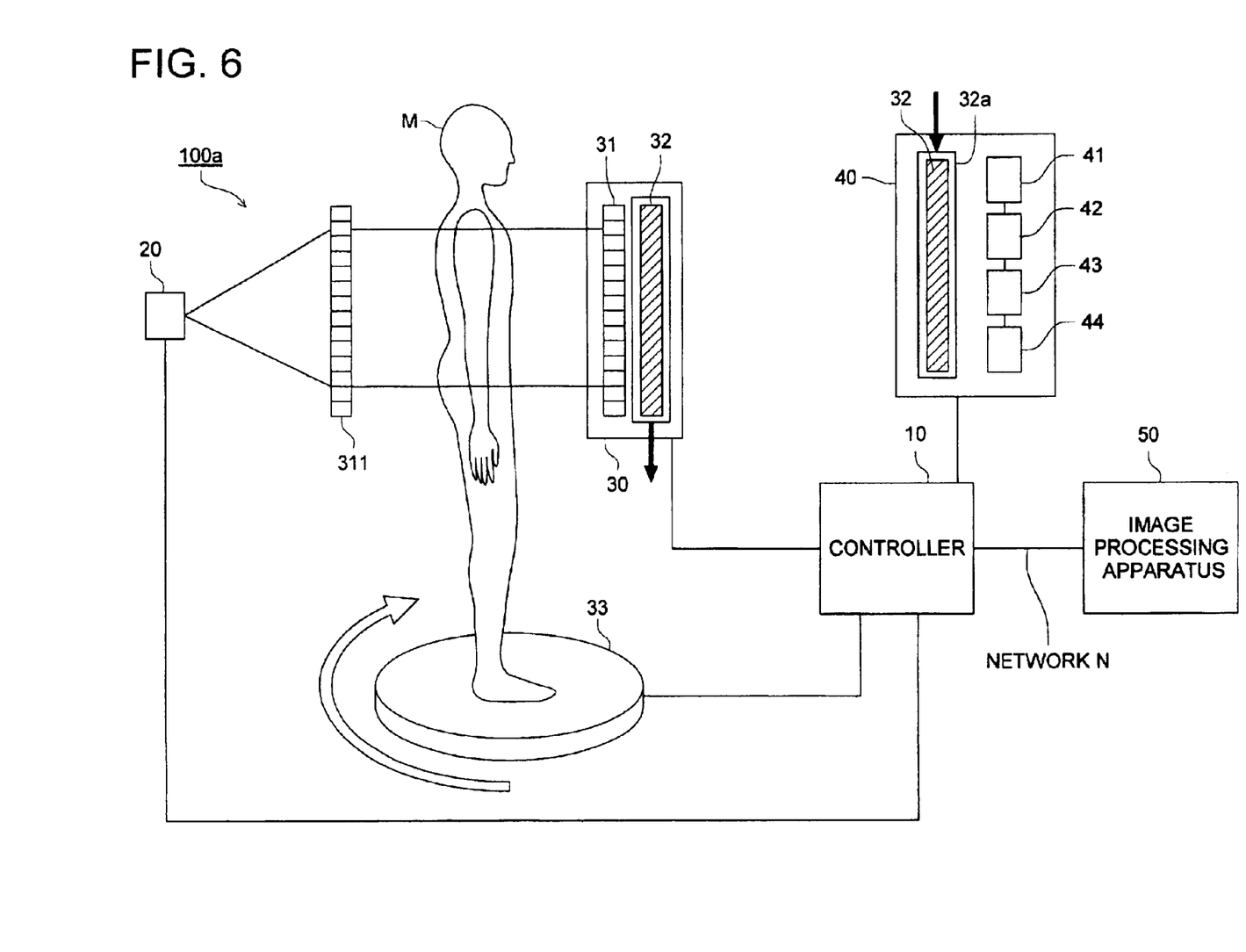
FIG. 6 is a drawing representing a radiographic image forming system 100a as another embodiment of the present invention.

In the above description, a cone beam of radiation is applied to the test body M, and is changed into a fan beam when the radiation passed through the slit shield plate 31. Without being restricted thereto, it is also possible that a slit shield plate 311—the same as slit shield plate 31—is installed between the radiation source 20 and test body M so that slit positions are matched, as shown in FIG. 6. Operation is performed synchronously with the slit shield plate 31, and the radiation is turned in a fan beam before a cone beam of radiation is applied to the test body M. This arrangement more effectively removes the scattered light that may be generated from the test body M and minimizes the exposure dose of the test body M.

In the above description, a cassette method was used, wherein a stimulable phosphor plate 32 is built in the cassette 32a, and the cassette 32a recording the sinogram is inserted into the radiation reading apparatus 40. Without being restricted thereto, it is also possible to utilize a built-in system consisting of a combination of a scanner and a reader where the slit shield plate 31 and stimulable phosphor plate 32 are built in the radiation reading apparatus 40.

In the above description, radiographing is performed at each rotary angle by rotation/displacement of a test body with the rotatable table 33. Any other method can be used if the outer periphery of the test body can be radiographed.

Further, detailed arrangements and operations of various apparatuses constituting the radiographic image forming system 100 in the present embodiment or their constituents thereof can be designed as appropriate without departing from the spirit of the present invention.

Effects of the Invention

According to the inventions described in the aforementioned arrangements (1), (2) and (15), conical radiation is applied to the test body by relative rotation and displacement of the test body and radiation source, and the radiation shield plate is moved along the body axis of the test body for each rotation and displacement. Then the radiation having passed through the test body and through the slits of the radiation shield plate is recorded on the stimulable phosphor plate as a sinogram along the body axis. The recorded sinogram is read and a two-dimensional or three-dimensional tomographic image is formed by its reconstruction. This arrangement provides a two-dimensional or three-dimensional tomographic image of high picture quality with reduced image noise resulting from scattered light, by using a CR apparatus in widespread use. It provides a low-cost and space-saving radiographic image forming apparatus characterized by improved diagnostic capacity.

According to the description in the aforementioned arrangement (3), a pair of radiation shield plates is installed between the radiation source and test body, and between the test body and the stimulable phosphor plate so that the slit positions are matched. The pair of radiation shield plates is synchronized for each rotation and displacement and is moved along the body axis of the test body. The radiation having passed through the test body and the slits of the pair of radiation shield plates is recorded on the stimulable phosphor plate as a transmission image for each rotation and displacement. This arrangement reduces the image noise caused by scattered light, and minimizes the exposure dose of the test body, thereby allow a high-quality two-dimensional and three-dimensional tomographic image to be produced.

According to the invention shown in arrangements (4) and (5), the traveling distance of the radiation shield plate along the body axis for each rotation and displacement is 0.2 mm or more, and a spacing between slits of the radiation shield plate is 5 mm or more. This arrangement ensures that each of multiple transmission images constituting the sinogram stored on the stimulable phosphor plate does not practically overlap the other. Hence it provides an adequate margin to the space for recording a transmission image for each rotation and displacement, thereby providing a two-dimensional and three-dimensional tomographic image of high picture quality.

According to the invention described in arrangements (6), (7) and (8), the image forming means is an image forming apparatus connected to a plurality of transfer means. It reconstructs each of the sinograms transferred via the network and forms each two-dimensional or three-dimensional tomographic image. It sends the image together with the input result of diagnosis via the network to the source from which the sinogram has been sent. This arrangement permits a shared use of the image forming apparatus for forming a two-dimensional or three-dimensional tomographic image, thereby ensuring a lower cost. This arrangement also provides the result of diagnosis together with the image, with the result that the diagnostic capacity is improved.

According to the invention described in arrangements (9) and (10), the test body is rotated without exceeding 360 degrees, and this action reduces the load of the test body and the installation space for the radiographic image forming apparatus.

According to the invention described in arrangements (11) and (12), radiation is applied intermittently every time the radiation source and test body are rotated and displaced by a predetermined amount. This arrangement minimizes the exposure dose of the test body. What is more, the predetermined amount of rotation and displacement does not exceed 10 degrees. This improves the resolution and provides a two-dimensional or three-dimensional image of high picture quality.

According to the invention described in arrangement (13), the radiation source is controlled to apply radiation synchronously with the heartbeat of a test body. This minimizes the variation within the body of the test body and provides recording of a sinogram consisting of transmission images under uniform conditions, thereby offering a two-dimensional or three-dimensional tomographic image of high picture quality.

According to the invention described in arrangement (14), the amount of radiation is controlled in response to the rotation and displacement. This makes it possible to record a sinogram where the amount of radiation is adjusted in response to changes in the thickness of the body of the test body resulting from the position for each rotation and displacement, thereby providing a two-dimensional or three-dimensional tomographic image of high picture quality.

What is claimed is:

1. A radiographic image forming apparatus comprising:
   a radiation source for irradiating conical radiation to a test body, the radiation source being in a fixed location;
   a stimulable phosphor plate, fixedly arranged opposite to the radiation source with the test body sandwiched in-between the stimulable phosphor plate and the radiation source, for recording an intensity of radiation having passed through the test body;
   a rotatable table for rotating the test body about a body axis with respect to the radiation source;
   a radiation shield plate having multiple slits orthogonal to the body axis of the test body, and being arranged between the test body and the stimulable phosphor plate;
   a moving section for moving the radiation shield plate along the body axis of the test body, for each partial rotation of the rotatable table;
   a controller for controlling radiation from the radiation source, and synchronizes the movement of the rotatable table and the radiation shield plate to form a sinogram of one or more slit images on one plate of the stimulable phosphor plate;
   a reading section for reading the sinogram; and
   an image processing section for forming a two-dimensional or a three-dimensional tomographic image by processing the sinogram read by the reading section.

2. The radiographic image forming apparatus of claim 1, wherein the moving section moves the radiation shield plate along the body axis of the test body for a travel distance of 0.2 mm or more for each partial rotation of the rotatable table.

3. The radiographic image forming apparatus of claim 1, wherein spacing between neighboring slits of the radiation shield plate is 5 mm or more.

4. The radiographic image forming apparatus of claim 1, further comprising a transmission section for transmitting the sinogram read by the reading section to an external equipment connected to a network; wherein the image processing section is an image processing apparatus connected via the network, and forms a two-dimensional or a three-dimensional tomographic image by reconstructing the sinogram transmitted through the transmission section.

5. The radiographic image forming apparatus of claim 4, wherein the radiographic image forming apparatus is connected to a plurality of transmission sections via the network, and forms a two-dimensional or a three-dimensional tomographic image by processing each of the sinograms transmitted through the plurality of transmission sections.

6. The radiographic image forming apparatus of claim 4, wherein the image processing apparatus comprises an input section for inputting a result of diagnosis of the two-dimensional or three-dimensional tomographic image,
   wherein the transmission section transmits the result of diagnosis together with the two-dimensional or three-dimensional tomographic image, via the network to a source from which the sinogram has been transmitted.

7. The radiographic image forming apparatus of claim 1, wherein an overall amount of rotation by the rotatable table does not exceed 360 degrees when rotating the test body with respect to the radiation source.

8. The radiographic image forming apparatus of claim 1, wherein the controller controls the application of radiation from the radiation source, and the moving section moves the radiation shield plate along the body axis of the test body each time test body is moved at predetermined amount of rotation by the rotatable table.

9. The radiographic image forming apparatus of claim 8, wherein the predetermined amount of rotation by the rotatable table does not exceed 10 degrees.

10. The radiographic image forming apparatus of claim 1, wherein the controller controls the application of radiation from the radiation source synchronously with a heartbeat of the test body.

11. The radiographic image forming apparatus of claim 1, wherein the controller controls the amount of radiation irradiated by the radiation source in accordance with the rotation made by the rotatable table.

12. A radiographic image forming apparatus comprising:
   a radiation source for irradiating conical radiation to a test body, the radiation source being arranged at a fixed position;

a stimulable phosphor plate, fixedly arranged opposite to the radiation source with the test body sandwiched in-between the stimulable phosphor plate and the radiation source, wherein the stimulable phosphor plate records an intensity of radiation that has passed through the test body;

a rotatable table for rotating the test body about a body axis with respect to the radiation source;

a pair of radiation shield plates, wherein each radiation shield plate comprises multiple slits orthogonal to the body axis of the test body, wherein one of the pair of radiation shield plates is located between the radiation source and the test body and the other of the pair of radiation shield plates is located between the test body and the stimulable phosphor plate, and wherein the pair of radiation shield plates is aligned in such a manner that the positions of the respective multiple slits of the pair of radiation shield plates coincide with each other;

a moving section for synchronizing and moving the pair of radiation shield plates along the body axis of the test body, for each partial rotation of the rotatable table; and a controller for controlling radiation from the radiation source, and synchronizes the movement of the rotatable table and the pair of radiation shield plates to form a sinogram of one or more slit images on one plate of the stimulable phosphor plate;

a reading section for reading the sinogram; and an image processing section for forming a two-dimensional or a three-dimensional tomographic image by processing the sinogram read by the reading section.

13. The radiographic image forming apparatus of claim 12, wherein the moving section moves the pair of radiation shield plates along the body axis of the test body for a travel distance of 0.2 mm or more for each partial rotation of the rotatable table.

14. The radiographic image forming apparatus of claim 12, wherein spacing between neighboring slits of the pair of radiation shield plates is 5 mm or more.

15. A method of radiographic image forming with an apparatus comprising:

a radiation source for directing conical radiation to a test body, the radiation source being fixedly arranged;

a stimulable phosphor plate, fixedly arranged opposite to the radiation source with the test body sandwiched in-between, for recording an intensity of radiation having passed through the test body; and a rotatable table for relatively rotating the test body about a body axis with respect to the radiation source, by placing the test body at a rotation center;

a radiation shield plate having a multiple slits orthogonal to the body axis of the test body, and being arranged between the test body and the stimulable phosphor plate; and a moving section for moving the radiation shield plate along the body axis of the test body, for each rotation by the rotatable table;

the method of radiographic image forming comprises:

controlling a radiation from the radiation source;

recording the radiation having passed through the test body and the slits of the radiation shield plate, into the stimulable phosphor plate, for each rotation by the rotatable table, as a transmitted image to form a sinogram of slit images on one plate of the stimulable phosphor plate;

reading the sinogram recorded; and forming a two-dimensional or three-dimensional tomographic image by reconstructing the sinogram read by the reading step.

16. A method of radiographic image forming comprising:

directing conical radiation from a radiation source to a test body, the radiation source being in a fixed location;

recording an intensity of radiation, having passed through the test body, on a stimulable phosphor plate fixedly arranged opposite to the radiation source, wherein the test body is located in between the stimulable phosphor plate and the radiation source;

rotating the test body about a body axis with respect to the radiation source through the use of a rotatable table;

locating a radiation shield plate having multiple slits orthogonal to the body axis of the test body between the test body and the stimulable phosphor plate;

moving the radiation shield plate along the body axis of the test body for each partial rotation of the rotatable table;

controlling the radiation produced from the radiation source;

recording the radiation having passed through the test body and the slits of the radiation shield plate into the stimulable phosphor plate for each partial rotation by the rotatable table, as a transmitted image to form a sinogram of one or more slit images on one plate of the stimulable phosphor plate;

reading the sinogram; and forming a two-dimensional or a three-dimensional tomographic image by processing the sinogram read by the reading step.

* * * * *